United States Patent [19]

Tujimoto et al.

[11] Patent Number: 5,378,616
[45] Date of Patent: Jan. 3, 1995

[54] MUTANT *ESCHERICHIA COLI* CAPABLE OF ENHANCED L-GLUTAMIC ACID PRODUCTION BY FERMENTATION

[75] Inventors: Nobuharu Tujimoto; Yoshimi Kikuchi; Osamu Kurahashi; Yoshiko Kawahara, all of Kawasaki, Japan

[73] Assignee: Ajinomoto Co., Inc., Tokyo, Japan

[21] Appl. No.: 925,651

[22] Filed: Aug. 7, 1992

[30] Foreign Application Priority Data

Aug. 7, 1991 [JP] Japan .................................. 3-197774

[51] Int. Cl.$^6$ .................. C12P 13/14; C12N 1/00; C12N 1/20
[52] U.S. Cl. ............................... 435/110; 435/252.8; 435/848; 435/849
[58] Field of Search .................. 435/252.5, 252.8, 110, 435/848, 849

[56] References Cited

FOREIGN PATENT DOCUMENTS 0030391 10/1980 European Pat. Off. .

OTHER PUBLICATIONS

*Biochemistry* Mathews and van Holde 1990 pp. 490–491.
*Biochemistry* Stryer 3rd Edition 1988 pp. 382–383.
Herbert et al. J. Gen Microbiol 53:pp. 363–381 1968.
Berberich Biochem. Biophy Res Comm 47:6 pp. 1498–1503 1972.
Pahel et al. J of Bacter 133:1 pp. 139–148 1978.
Isamu Shiio et al, "Significance of α-Ketoglutaric Dehydrogenase on the Glutamic Acid Formation in Brevibacterium Flavum," The Journal of Biochemistry., vol. 50, No. 2, pp. 164–165 (1961).
A. A. Herbert et al, "Studies With α-Ketoglutarate Dehydrogenase Mutants of *Escherichia coli*," Molec. Gen. Genetics, vol. 105, pp. 182–190 (1969).
C. B. Brice et al, "Genetic Control of Isocitrate Lyase Activity in *Escherichia coli*," Journal of Bacteriology, vol. 96, No. 6, pp. 2185–2186 (Dec. 1968).
Joshua Lederberg et al, "Replica Plating and Indirect Selection of Bacterial Mutants," vol. 63 (1952), pp. 399–406.
E. Vanderwinkel et al, "Genetic Control of the Regulation of Isocitritase and Malate Synthase in *Escherichia coli* K 12," Biochemical and Biophysical Research Communications, vol. 12, No. 2 (1963), pp. 157–162.
Lester J. Reed et al, "α-Ketoglutarate Dehydrogenase Complex From *Escherichia coli*," Methods in Enzymology, vol. 13, (1969), pp. 55–61.
The Journal of Biochemistry, vol. 50, No. 2, 1961, Tokyo JP pp. 164–165 Isamu Shiio et al 'Significance of alpha–ketoglutaric dehydrogenase on the glutamic acid formation in *Brevibacterium flavum*'. ·
Molecular and General Genetics, vol. 105, 1969, pp. 182–190 A. A. Herbert et al 'Studies with alpha–Ketoglutarate Dehydrogenase mutants of *Escherichia coli*'.

*Primary Examiner*—David M. Naff
*Assistant Examiner*—Deborah K. Ware
*Attorney, Agent, or Firm*—Oblon, Spivak, McClelland, Maier & Neustadt

[57] ABSTRACT

The present invention provides a mutant and a process for producing L-glutamic acid by fermentation using a microorganism belonging to the genus Escherichia. In the present process, L-glutamic acid is produced and accumulated in a culture medium by (A) culturing an Escherichia mutant which is deficient or low in α-ketoglutaric acid dehydrogenase activity, has low L-glutamic acid decomposing ability, and is capable of producing L-glutamic acid.

2 Claims, No Drawings

MUTANT ESCHERICHIA COLI CAPABLE OF ENHANCED L-GLUTAMIC ACID PRODUCTION BY FERMENTATION

BACKGROUND OF THE INVENTION

1. Field of the Invention

The present invention relates to a mutant *Escherichia coli* capable of enhanced L-glutamic acid production and a process for producing L-glutamic acid by fermentation. L-glutamic acid is an amino acid which is important as food, medicine, etc.

2. Discussion of the Background

Heretofore, glutamic acid has been produced by fermentation using a glutamic acid-producing bacterium belonging to the genera Brevibacterium, Corynebacterium or Microbacterium ("Amino Acid Fermentation, pp." 195–215, published by Gakkai Shuppan Center, (1986)). Other known processes for fermentatively producing L-glutamic acid employ microorganisms belonging to the genera Bacillus, Streptomyces, Penicillium (U.S. Patent No. 3,220,929) or the genera Pseudomonas, Arthrobacter, Serratia or Candida (U.S. Pat. No. 3,563,857). By these processes, L-glutamic acid can be produced with a fairly high productivity. However, in order to meet ever-increasing demand for the amino acid, a more effective and less costly process is desired.

With its fast growth and the advancement in the analysis of its gene, *Escherichia coli* has potential as a good L-glutamic acid-producing microorganism. However, according to published reports, *Escherichia coli* accumulates L-glutamic acid at only an extremely low level, not higher than 2.3 g/l (*J. Biochem.*, vol. 50, p. 164–165 (1961)).

SUMMARY OF THE INVENTION

Accordingly, one object of the present invention is to provide a more effective and less costly a process for producing L-glutamic acid by fermentation.

Another object of the present invention is to provide a mutant *Escherichia coli* capable of enhanced L-glutamic acid production.

Another object of the present invention is to provide a process for producing L-glutamic acid using microorganisms belonging to the genus Escherichia.

These and other objects which will become apparent from the following detailed description of the preferred embodiments have been achieved by a mutant *Escherichia coli*, which (1) is deficient or low in α-ketoglutaric acid dehydrogenase (hereinafter referred to as "α-KGDH") activity, (2) is low in L-glutamic acid decomposition activity and (3) has the ability to produce L-glutamic acid, and a process for the production of L-glutamic acid using a mutant *Escherichia coli* capable of enhanced L-glutamic acid production.

DETAILED DESCRIPTION OF THE PREFERRED EMBODIMENTS

The present inventors have conducted intensive studies on the production of L-glutamic acid using mutants of *Escherichia coli*. As a result, certain mutants of *Escherichia coli* which (1) are deficient or low in α-ketoglutaric acid dehydrogenase (hereinafter referred to as "α-KGDH") activity, (2) are low in L-glutamic acid decomposition activity and (3) have the ability to produce L-glutamic acid, as well as mutants of *Escherichia coli* which have the above properties and which also express malate synthase (ace B), isocitrate lyase (ace A) and isocitrate dehydrogenase kinase/phosphatase (ace K) operons (hereinafter referred to as the "ace operon") possess the potential to produce increased amounts of L-glutamic acid.

Accordingly, the present invention provides a process for producing L-glutamic acid by fermentation, which comprises (A) culturing in a liquid medium a mutant which belongs to the genus Escherichia, said mutant being (i) deficient or low in α-KGDH activity, (ii) low in glutamic acid dehydrogenase activity and (iii) able to produce L-glutamic acid; and (B) recovering the compound from the culture medium. The present invention also provides a process for producing L-glutamic acid by fermentation which comprises (A) culturing in a liquid medium a mutant which (a) belongs to the genus Escherichia, (b) is deficient or low in α-KGDH activity, (c) is low in glutamic acid decomposition activity, (d) has the ability of producing L-glutamic acid, and (e) which constitutively expresses the ace operon; and (B) recovering the compound from the culture medium. Preferably, L-glutamic acid is accumulated in the culture medium during the culturing step in the above processes.

In addition to the above properties, the mutants may be provided with other properties known to be effective for improving L-glutamic acid-producing ability, such as certain requirements for various nutrients, drug resistance, drug sensitivity, drug dependence, and the like. As examples of mutants according to the invention, mention may be made of the following:

*Escherichia coli* AJ 12628 (FERM P-12380)
*Escherichia coli* AJ 12624 (FERM P-12379)

As a parent for introducing a mutant according to the invention, there can be used microorganisms which belong to the genus Escherichia and which are non-pathogenic. As examples of such microorganism, mention may be made of the following strains:

Escherichia coli K-12 (ATCC 10798)
Escherichia coli W-3110 (ATCC 27325)

Mutants according to the invention can be obtained by applying to such parent strains a conventional mutation-inducing technique. For example, irradiation of the microorganisms with X-rays or ultraviolet rays, or contact with a mutagen, such as N-methyl-N'-nitro-N-nitrosoguanidine (hereinafter referred to as "NG") are suitable methods of inducing mutations. Such mutants can also be produced by other genetic techniques, such as gene recombination, transduction, cell fusion, and the like.

More specifically, mutants can be obtained, e.g., in the following manner:

Mutants deficient or low in α-KGDH activity can be obtained, for example, as a strain which is incapable of growth or which grows extremely slowly in a glucose-containing minimal medium under aerobic culture conditions, but is capable of growth in a glucose-containing medium to which is added (1) succinic acid or (2) lysine and methionine. Alternatively, the mutant can be a strain which is capable of growth in a glucose-containing minimal medium under anaerobic culture conditions (*Molec. Gen. Genetics*, vol. 105, p. 182–190, (1969)).

Mutants which constitutively express the ace operon can be obtained by using a phosphoenolpyruvate synthase (pps) deficient strain as a parent. The desired mutants can be obtained as a strain capable of growth in a minimal medium containing lactic acid as a carbon source but which are incapable of growth in a minimal medium containing pyruvic acid (which may also contain acetic acid) as a carbon source (*J. Bacteriol.*, vol. 98, p. 2185–2186 (1968)). Such mutants can also be obtained as a variant capable of improving the growth of strains which are deficient or low in α-KGDH activity under aerobic culture conditions.

Mutants which have low L-glutamic acid decomposing ability can be isolated as a strain incapable of or extremely slow in growing in a minimal medium containing L-glutamic acid as either the sole carbon source (in place of glucose) or as the sole nitrogen source (in place of ammonium sulfate). When a variant that requires certain nutrients is used, the minimum quantity of nutrients required for the growth of the mutants must be added to the medium.

The thus-obtained mutants of the present invention are provided with an improved ability to biosynthetically produce L-glutamic acid via α-ketoglutaric acid in the TCA cycle. The mutants have an improved ability for producing L-glutamic acid since they are extremely low in the activity of decomposing L-glutamic acid, or are incapable of decomposing L-glutamic acid. Additionally, their growth is improved due to constitutive expression of the ace operon.

By using the thus-obtained variants, L-glutamic acid can be produced in accordance with conventional fermentation procedures in conventional nutrient media containing carbon sources, nitrogen sources, inorganic salts and, where necessary, minor organic nutrients, such as amino acids, vitamins, and the like. Both synthetic and natural media can be used.

Any carbon and nitrogen sources can be used, provided that the mutants can assimilate the carbon and nitrogen sources used. Examples of suitable carbon sources include saccharides, such as glucose, glycerol, fructose, sucrose, maltose, mannose, galactose, hydrolyzed products of starch, and molasses. It is also possible to use organic acids, such as acetic acid and citric acid, either alone or in combination with other carbon sources. Examples of suitable nitrogen sources include ammonia, ammonium sulfate, ammonium carbonate, ammonium chloride, ammonium phosphate and ammonium acetate. Examples of minor organic nutrients include amino acids, vitamins, fatty acids and nucleic acids. It is also possible to use other materials that contain such nutrients, for example, peptone, casamino acids (acid-hydrolyzed casein), yeast extract, and hydrolyzed products of soybean proteins. Where a variant (*E. coli* mutant) requires amino acids for its growth, the nutrients required by the variant or mutant must be supplemented in the culture medium for its proper use. Examples of usable inorganic salts include alkali metal and alkaline earth phosphates, biologically acceptable magnesium salts, calcium salts, iron salts, manganese salts, and the like.

Culturing of the microorganism can be carried out with aeration under controlled conditions (e.g., at a temperature of from 20° to 45° C. and a pH of from 5 to 9). If the pH drops during culturing, the culture medium may be neutralized, e.g., by sufficient amounts of calcium carbonate, ammonia gas or solutions thereof to adjust the pH to a biologically acceptable level. Thus, a large quantity of L-glutamic acid can be accumulated in the medium within about 10 hours to 4 days.

After culturing is complete, L-glutamic acid is recovered from the medium in accordance with one or more known procedures. For example, after the removal of the cells by filtration, ultrafiltration, centrifugation or other known means, glutamic acid is recovered by, for example, concentration of the cell-free solution and crystallization of the glutamic acid (or a salt thereof). Alternatively, the compound can be recovered by ion exchange chromatography.

Other features of the present invention will become apparent in the course of the following descriptions of exemplary embodiments which are given for illustration of the invention, and are not intended to be limiting thereof.

EXAMPLE 1

Induction of a Variant Having a Low L-Glutamic Acid Decomposition Activity

*Escherichia coli* W3110 was cultured at 37° C. for 3 hours in an L-broth containing 0.5% of yeast extract, 1% of polypeptone and 0.5% of sodium chloride (pH 7.0). The living o cells of the microorganism were treated with N-methyl-N'-nitro-N-nitrosoguanidine (NG) at a concentration of 500 μg/ml at 37° C. for 15 minutes to induce mutation. Using the basal minimum medium, minimal medium (A) containing L-glutamic acid as the sole carbon source and minimal medium (B) containing L-glutamic acid as the sole nitrogen source (detailed in Table 1 below), the treated cells were examined in accordance with the replica method to obtain a mutant, *Escherichia coli* GH-1, which was capable of growth in the basal minimal medium, but grew extremely slowly in both minimal medium (A) and minimal medium (B) (culturing temperature, 37° C; culturing period, 2 days).

TABLE 1

| | Concentration of Media Components (in g/l) | | | | |
|---|---|---|---|---|---|
| | Basal Minimal Medium | Minimal Medium (A) | Minimal Medium (B) | Minimal Medium (C) | Minimal Medium (D) |
| Glucose | 5 | — | 5 | 5 | 5 |
| $NH_4Cl$ | 1 | 1 | — | 1 | 1 |
| $Na_2HPO_4.7H_2O$ | 12.8 | 12.8 | 12.8 | 12.8 | 12.8 |
| $KH_2PO_4$ | 3 | 3 | — | 3 | 3 |
| NaCl | 0.5 | 0.5 | — | 0.5 | 0.5 |
| $MgSO_4.7H_2O$ | 0.2 | 0.2 | 0.2 | 0.2 | 0.2 |
| L-Glutamic acid | — | 2.0 | 3.5 | — | — |
| Succinic acid | — | — | — | 6 | — |
| L-Lysine | — | — | — | — | 0.1 |
| L-Methionine | — | — | — | — | 0.1 |

In order to examine the L-glutamic acid decomposition activity of the mutant *Escherichia coli* GH-1 and its parent, *Escherichia coli* W3110, samples of each microorganism were cultured at 37° C. for 48 hours in each of the liquid media described in Example 1 and detailed in Table 1 above. Results obtained are shown in Table 2 below.

*Escherichia coli* GH-1 exhibited extremely poor growth in both minimal medium (A) containing L-glutamic acid as the sole carbon source and minimal medium (B) containing L-glutamic acid as the sole nitrogen source, and was low in L-glutamic acid metabolism, compared with its parent.

TABLE 2

| Medium | W3110 (OD660) | GH-1 (OD660) |
|---|---|---|
| Basal Minimal Medium | 0.80 | 0.65 |
| Minimal Medium (A) | 0.45 | 0.07 |
| Minimal Medium (B) | 0.80 | 0.15 |

(Data represent turbidity at 660 nm)

EXAMPLE 2

Induction of a Variant Deficient or Low in α-KGDH Activity

*Escherichia coli* GH-1 obtained as described in Example 1 above was subjected to a second mutation in the same manner as described in Example 1 above to obtain a second mutant, *Escherichia coli* AJ12628, which grew extremely slowly in the basal minimal medium shown in Table 1 (as determined by the replica method), but grew well in both minimal medium (C) containing succinic acid and minimal medium (D) containing L-lysine and L-methionine, detailed in Table 1 above (culturing temperature, 37° C.; culturing period, 2 days).

For the purpose of comparison, the α-KGDH activity of the mutant *Escherichia coli* AJ 12628 and that of *Escherichia coli* W3110 were determined by the method of Reed et al ("Methods in Enzymology," vol. 13, p. 55, (1969)). Results obtained are shown in Table 3.

*Escherichia coli* AJ12628 exhibited no detectable α-KGDH activity, whereas grandparent strain *Escherichia coli* W3110 exhibited substantial α-KGDH activity.

TABLE 3

|  | W3110 | AJ12628 |
|---|---|---|
| α-KGDH Activity | 3.70 | Not Detected |

(Unit: μmoles/mg protein/min)

EXAMPLE 3

Induction of a Variant Which Constitutively Expresses the Ace Operon

*Escherichia coli* AJ12628 was transduced with the ic1R marker by the P1vir phage, using as a donor *Escherichia coli* PLK831 (ic1R7, gal, trpE, pyrF, fnr, rpsL, trpR), a strain which constitutively expresses the ace operon (the strain was obtained from *E. coli* Genetic Stock Center, Yale University, U.S.A.). Calcium chloride was added at a concentration of $2.5 \times \times 10^{-3}$M to a culture of *Escherichia coli* PLK831, cultivated up to a logarithmic growth phase. P1vir was then added thereto up to an m.o.i. (multiplicity of infection, i.e., number of phages per cell) of 5, and the cultivation was continued at 37° C. for 90 minutes, to obtain a bacteriolytic solution. To this solution was added chloroform to kill remaining bacteria. The resulting solution was centrifuged to produce a supernatant, i.e., a phage solution.

*Escherichia coli* AJ12628 was separately cultured in the L-broth of Example 1 above up to a logarithmic growth phase. Calcium chloride was then added to this culture at the same concentration as above. Subsequently, sufficient phage solution was added to result in an m.o.i. of 0.2, and the resulting solution was allowed to stand at 37° C. for 30 minutes and then centrifuged to remove the supernatant. Cells obtained were suspended into a physiological salt solution containing $2.5 \times 10^3$M of $CaCl_2$, and inoculated onto a plate filled with minimal medium (D), described in Table 1. The cells were cultivated at 37° C. for 2 days to obtain *Escherichia coli* AJ12624 as a strain capable of faster growth than *Escherichia coli* AJ12628.

The two strains were separately cultivated in liquid medium (D) under aerobic conditions, and the isocitrate lyase activity of each strain was determined according to the method of Vanderwinkel et al (*Biochem. Biophys. Res. Commun.*, vol. 12, p. 157, (1963)). Results obtained are shown in Table 4.

As is seen from the table, *Escherichia coli* AJ12624 has an extremely enhanced isocitrate lyase activity. This shows that the ace operon of this strain is constitutively expressed as a result of transduction.

TABLE 4

|  | AJ12628 | AJ12624 |
|---|---|---|
| Isocitrate Lyase Activity | 6 | 90 |

(Unit: μmoles/mg protein/min)

Example 4

Production of L-Glutamic Acid by the Mutant Obtained

Each of the *Escherichia coli* strains W3110, GH-1, AJ12628 and AJ12624 was inoculated separately into a 500 ml flask, each flask containing 20 ml of medium having a composition as shown in Table 5. Each of the strains was shake-cultured at 37° C. until the glucose was consumed. L-Glutamic acid was accumulated in the quantities shown in Table 6.

TABLE 5

| Component | Concentration (g/l) |
|---|---|
| Glucose | 40 |
| $(NH_4)_2SO_4$ | 20 |
| $KH_2PO_4$ | 1 |
| $MgSO_4.7H_2O$ | 1 |
| $FeSO_4.7H_2O$ | 0.01 |
| $MnSO_4.5H_2O$ | 0.01 |
| Yeast extract | 2 |
| L-Methionine | 0.1 |
| L-Lysine | 0.1 |

TABLE 6

| Strain | Amount of L-glutamic Acid Accumulated (g/L) | Period of Fermentation (hr) |
|---|---|---|
| W3110 | 3.0 | 12 |
| GH-1 | 5.0 | 15 |
| AJ12628 | 18.5 | 27 |
| AJ12624 | 20.0 | 16 |

The results in Table 6 above show that the amount of L-glutamic acid accumulated in the culture medium is markedly increased by use of a mutant which (A) is deficient in α-KGDH activity, (B) low in ability to decompose L-glutamic acid and (c) capable of producing L-glutamic acid (e.g., *E. coli* AJ12628 and *E. coli* AJ12624). In addition, the fermentation period can be markedly shortened by use of a mutant having the above characteristics, and which constitutively expresses the ace operon (e.g., *E. coli* AJ12624).

EXAMPLE 5

Cultivation of AJ12628 and AJ12624 in a Medium Without Succinic Acid or a Mixture of L-Lysine and L-Methionine Each of the *Escherichia coli* strains AJ12628 and AJ12624 was inoculated separately into each of four 500 ml flasks, each flask separately containing 20 ml of one of the media A, B, C and D, having the compositions shown in Table 7 below. Each of the strains was shake-cultured at 37° C. until the glucose was consumed. L-Glutamic acid was accumulated in the quantities shown in Table 8. Medium B in Table 7 is the same as the medium described in Table 5.

TABLE 7

| | Concentration (g/l) | | | |
|---|---|---|---|---|
| Component | medium A | medium B | medium C | medium D |
| Glucose | 40 | 40 | 40 | 40 |
| (NH4)2SO4 | 20 | 20 | 20 | 20 |
| KH3PO4 | 1 | 1 | 1 | 1 |
| MgSO4.7H2O | 1 | 1 | 1 | 1 |
| FeSO4.7H2O | 0.01 | 0.01 | 0.01 | 0.01 |
| MnSO4.7H2O | 0.01 | 0.01 | 0.01 | 0.01 |
| Yeast extract | 2 | 2 | 2 | 2 |
| L-methionine | — | 0.1 | 0.5 | — |
| L-lysine | — | 0.1 | 0.5 | — |
| succinic acid | — | — | — | 1 |
| CaCO3 | 30 | 30 | 30 | 30 |

TABLE 8

| Strain | medium | Amount of L-glutamic Acid Accumulated (g/l) | Period of Fermentation (hr) |
|---|---|---|---|
| AJ12628 | A | 18.0 | 36 |
| | B | 18.5 | 27 |
| | C | 18.5 | 17.5 |
| | D | 19.5 | 18 |
| AJ12624 | A | 19.0 | 16.5 |
| | B | 20.0 | 16 |
| | C | 20.0 | 16 |
| | D | 20.5 | 16 |

As shown in Table 8, the period of fermentation using *E. coli* AJ12628, in which the ace operon is not expressed constitutively, was substantially shortened when a medium containing succinic acid or a mixture of L-lysine and L-methionine was used. On the other hand, the period of fermentation using *E. coli* AJ12624, in which the ace operon is expressed constitutively, was shortened considerably compared to fermentation using *E. coli* AJ12628 when succinic acid or a mixture of L-lysine and L-methionine is absent (Table 8, medium A). *E. coli* AJ12624 grows faster than *E. coli* AJ12628, even in medium A.

These results show that constitutive expression of the ace operon leads to a shortening of fermentation period of a strain of *E. coli* deficient or low in α-KGDH activity in a medium without succinic acid or a mixture of L-lysine and L-methionine.

When the ace operon is expressed constitutively, it is possible to use a simpler and less expensive medium, because the addition of succinic acid or a mixture of L-lysine and L-methionine is not required for growth of the microorganism.

In summary, the present invention provides an Escherichia mutant having improved L-glutamic acid producing capability. Further, L-glutamic acid can be produced in an effective manner at a lower cost using the present mutant.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing L-glutamic acid by fermentation which comprises:
    (A) culturing in a culture medium, a mutant which is derived from *Escherichia coli* K-12 strain, wherein said mutant (i) is deficient or low in α-KGDH activity, (ii) is low in glutamic acid decomposition activity, (iii) is able to produce L-glutamic acid and (iv) expresses a malate synthase, an isocitrate lyase and an isocitrate dehydrogenase kinase/phosphatase; and
    (B) isolating L-glutamic acid from the culture medium.

2. A process of claim 1, wherein said mutant is FERM P-12379.

* * * * *

UNITED STATES PATENT AND TRADEMARK OFFICE
CERTIFICATE OF CORRECTION

PATENT NO. : 5,378,616
DATED : January 3, 1995
INVENTOR(S) : Nobuharu TUJIMOTO et al It is certified that error appears in the above-identified patent and that said Letters Patent is hereby corrected as shown below:

Column 4, line 33, "living o cells" should read --living cells--.

Column 5, line 56, "2.5X X10$^{-3}$M" should read --2.5X10$^{-3}_{M}$--.

Signed and Sealed this

Twenty-fourth Day of September, 1996

Attest:

BRUCE LEHMAN

Attesting Officer     Commissioner of Patents and Trademarks